(12) United States Patent
Engel

(10) Patent No.: US 7,382,857 B2
(45) Date of Patent: Jun. 3, 2008

(54) X-RAY CATHETER ASSEMBLY

(75) Inventor: Thomas Engel, Erfurt (DE)

(73) Assignee: Carl Zeiss AG (DE)

( * ) Notice: Subject to any disclaimer, the term of this patent is extended or adjusted under 35 U.S.C. 154(b) by 0 days.

(21) Appl. No.: 11/009,910

(22) Filed: Dec. 10, 2004

(65) Prior Publication Data
US 2006/0126788 A1 Jun. 15, 2006

(51) Int. Cl.
*A61N 5/10* (2006.01)
(52) U.S. Cl. .......................... 378/65; 378/119
(58) Field of Classification Search ................ 378/119, 378/64–65, 121–122; 600/3, 433–445
See application file for complete search history.

(56) References Cited

U.S. PATENT DOCUMENTS

| | | | | |
|---|---|---|---|---|
| 4,195,637 | A | * | 4/1980 | Gruntzig et al. ............. 604/509 |
| 5,053,033 | A | * | 10/1991 | Clarke ............................ 606/3 |
| 5,153,900 | A | | 10/1992 | Nomikos et al. ............. 378/65 |
| 5,246,421 | A | * | 9/1993 | Saab ........................... 606/194 |
| 5,369,679 | A | | 11/1994 | Sliski et al. .................. 378/65 |
| 5,422,926 | A | | 6/1995 | Smith et al. ................. 378/121 |
| 5,428,658 | A | | 6/1995 | Oettinger et al. ............ 378/119 |
| 5,566,221 | A | | 10/1996 | Smith et al. ................. 378/145 |
| 5,621,780 | A | | 4/1997 | Smith et al. .................. 378/65 |
| 5,913,813 | A | | 6/1999 | Williams et al. ............... 600/3 |
| 5,931,774 | A | | 8/1999 | Williams et al. ............... 600/2 |
| 6,022,308 | A | | 2/2000 | Williams ........................ 600/2 |
| 6,036,631 | A | * | 3/2000 | McGrath et al. ............... 600/3 |
| 6,083,148 | A | | 7/2000 | Williams ........................ 600/2 |
| 6,148,061 | A | | 11/2000 | Shefer et al. | 
| 6,319,188 | B1 | * | 11/2001 | Lovoi ............................. 600/3 |
| 6,320,935 | B1 | | 11/2001 | Shinar et al. |
| 6,324,257 | B1 | | 11/2001 | Halavee |
| 6,390,967 | B1 | * | 5/2002 | Forman et al. ................ 600/3 |

(Continued)

FOREIGN PATENT DOCUMENTS

EP 1 230 950 A 8/2002

OTHER PUBLICATIONS

International Search Report mailed Jun. 23, 2006, based on International Application: PCT/IB2005/004082.

(Continued)

*Primary Examiner*—Edward J. Glick
*Assistant Examiner*—John M Corbett
(74) *Attorney, Agent, or Firm*—Mark G. Lappin; Foley & Lardner LLP

(57) ABSTRACT

An apparatus for applying x-rays to an interior surface of a body cavity includes a catheter assembly, and one or more flexible probe assemblies. An x-ray generator assembly, including an optically activated x-ray source, is coupled to a distal end of each flexible probe assembly. The catheter assembly includes a body member defining one or more interior channels; an x-ray absorption control layer surrounding the body member; at least one inner tube enclosing the body member and the absorption control layer; at least one outer tube; and one or more inflatable elements coupled to the inner tube. The inflatable elements, when inflated, fixedly position the catheter assembly within the body cavity. Each flexible probe assembly is slidably positionable within at least one of the interior channels, and includes a transmission path adapted to transmit an activating energy, such as light from laser, onto a cathode within the x-ray source.

43 Claims, 11 Drawing Sheets

U.S. PATENT DOCUMENTS

| | | |
|---|---|---|
| 6,480,568 B1 | 11/2002 | Dinsmore ............... 378/65 |
| 6,496,561 B1 * | 12/2002 | Meyer et al. ............ 378/65 |
| 6,524,302 B2 * | 2/2003 | Kelley ................... 604/523 |
| 6,540,655 B1 | 4/2003 | Chin et al. |
| 6,561,966 B1 * | 5/2003 | Smith et al. ............ 600/3 |
| 6,587,709 B2 * | 7/2003 | Solf et al. .............. 600/424 |
| 6,894,261 B2 * | 5/2005 | Castenmiller et al. ... 250/208.1 |
| 6,987,835 B2 | 1/2006 | Lovoi |
| 2002/0191745 A1 | 12/2002 | Dinsmore |
| 2003/0032851 A1 * | 2/2003 | Apple et al. ............ 600/3 |
| 2003/0128808 A1 * | 7/2003 | Kindlein et al. ........ 378/65 |
| 2003/0179854 A1 * | 9/2003 | Jaafar .................... 378/119 |
| 2005/0080313 A1 * | 4/2005 | Stewart et al. .......... 600/3 |
| 2005/0080340 A1 | 4/2005 | Stewart et al. |
| 2005/0226378 A1 | 10/2005 | Cocks et al. |
| 2006/0078087 A1 * | 4/2006 | Forman et al. .......... 378/65 |

OTHER PUBLICATIONS

International Search Report mailed May 2, 2006, based on International Application: PCT/US05/32849.

* cited by examiner

X-RAY CATHETER ASSEMBLY

BACKGROUND

X-ray radiation applied to the interior of a patient's anatomical structure, for example to the soft tissue lining a body cavity of the patient, is known to be useful in the treatment of tumors. Diseases other than tumors can be treated in a similar manner, for example x-rays can be applied to the interior of blood vessels in order to prevent restenosis. In these and other treatments, most conventional x-ray therapy utilizes an external radiation source which directs relatively high energy x-rays toward the patient. The x-rays must first penetrate the skin and other tissue disposed between the x-ray radiation source and the target tissue, prior to reaching the tissue lining the body cavity. The exposure to such x-rays often causes significant damage to the skin and the tissue between the x-ray source and the target tissue.

Brachytherapy, on the other hand, is a form of treatment in which the source of radiation is located close to or in some cases within the area receiving treatment. The term brachytherapy has commonly been used to describe the use of radioactive "seeds," i.e. encapsulated radioactive isotopes which can be placed directly within or adjacent the target tissue to be treated. Handling and disposal of such radioisotopes, however, may impose considerable hazards to both the handling personnel and the environment.

The term "x-ray brachytherapy" is defined in the present application as an x-ray radiation treatment in which the x-ray source is located close to or within the area receiving treatment. X-ray brachytherapy typically involves positioning an insertable probe into or adjacent to the tumor, or into the site where the tumor or a portion of the tumor was removed, to treat the tumor or the tissue adjacent the site with a local boost of radiation. X-ray brachytherapy devices generally include a miniaturized low power radiation source, which can be inserted into, and activated from within, a patient's body. In x-ray brachytherapy, therefore, x-rays can be applied to treat a predefined tissue volume without significantly affecting the tissue adjacent to the treated volume. Also, x-rays may be produced in predefined dose geometries disposed about a predetermined location. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy systems are disclosed, by way of example, in U.S. Pat. No. 5,153,900 issued to Nomikos et al. ("the '900 patent"), U.S. Pat. No. 5,369,679 to Sliski et al. ("the '679 patent"), U.S. Pat. No. 5,422,926 to Smith et al. ("the '926 patent"), and U.S. Pat. No. 5,428,658, to Oettinger et al. ("the '658 patent"), all of which are owned by the assignee of the present application, and all of which are hereby incorporated by reference in their entireties. The x-ray brachytherapy systems disclosed in the above-referenced patents include a miniaturized, insertable probe, which emits low power x-rays from a nominal "point" source located within or adjacent to the desired region to be affected. For example, the x-ray probe assembly disclosed in the '900 patent includes a housing, and a hollow, tubular probe extending from the housing and having an x-ray emitting target at its distal end. The probe encloses an electron source (such as a thermionic cathode) for generating electrons that are accelerated so as to strike the x-ray target. The x-ray brachytherapy device disclosed in the '658 patent includes a flexible x-ray probe, for example a flexible fiber optic cable enclosed within a metallic sheath, and uses a photocathode as the electron source. The flexible fiber optic cable couples light from a laser source or a light emitting device to the photocathode, which generates free electrons (due to the photoelectric effect) when irradiated by the light from the light source.

A number of patents describe x-ray brachytherapy systems which can produce x-rays in predefined dose geometries disposed about a predetermined location. U.S. Pat. No. 5,621,780 (hereinafter the "'780 patent")(commonly owned by the assignee of the present application and hereby incorporated by reference in its entirety) discloses an apparatus and method for irradiating a surface defining a body cavity in accordance with a predetermined dose distribution. The '926 patent discloses an apparatus and method for irradiating a volume in accordance with a predetermined dose distribution. In particular, the '926 patent discloses a variable transmission shield which is adapted to control the position of the isodose surfaces of the x-rays emitted from an x-ray target element.

When thermionic cathodes are used in x-ray brachytherapy devices, it is desirable that the cathode be heated as efficiently as possible, namely that the thermionic cathode reach as high a temperature as possible using as little power as possible. In conventional thermionic cathodes, a filament is heated resistively with a current, which in turn heats the cathode so that electrons are generated by thermionic emission. These types of cathodes frequently encounter a number of problems, for example: 1) thermal vaporization of the cathode filament, resulting in tube failure; and 2) degradation in the x-ray output due to heating of the anode and resulting localized surface melting and pitting. While a photocathode avoids such problems, it is difficult to fabricate photocathodes in the vacuum.

The '568 patent discloses a miniature therapeutic radiation source that uses a laser-heated thermionic cathode, which overcomes the problems described in paragraph 6 above. The laser-heated thermionic cathode disclosed in the '568 patent provides a reduced-power, increased efficiency electron source for the x-ray source. The '568 patent discloses that by using laser energy to heat the electron emissive surface of a thermionic cathode, instead of resistively heating the cathode, electrons can be generated with minimal heat loss, and with significantly reduced power requirements.

Because of the advantages of x-ray brachytherapy, described in paragraph 3, it is desirable to use x-ray brachytherapy to treat the soft tissue that lines body cavities. It is also desirable to establish a uniform or other desired contoured dose of radiation to the target tissue, using x-ray brachytherapy devices. For this purpose, an x-ray brachytherapy system is needed which can be easily inserted into an interior body cavity, and can be easily controlled and maneuvered while in operation within the cavity. In some cases, it is desirable that radiation treatment of the tissue lining the interiors of a body cavity provides the same dose of radiation to every segment of the tissue, i.e. a uniform dose. In other cases, specifically contoured non-uniform doses may be desired.

For these reasons, it is desirable to provide a low power, miniaturized x-ray brachytherapy system, which is implantable within a body cavity of a patient or attached adjacent to a desired anatomical region of a patient, so that tissue forming the anatomical region or tissue lining the body cavity can be directly irradiated with x-rays. In particular, it is desirable to provide an implantable and easily controllable x-ray brachytherapy system that can use an optically activated electron source, because of the associated advantages set forth in paragraph 7. It is further desirable that such a miniaturized x-ray brachytherapy system be operable to irradiate a selected volume of a desired anatomical region, and to establish an absorption profile defined by predetermined isodose contours. It is further desirable that the miniaturized x-ray brachytherapy device be operable to provide a uniform, or other desired, dose of x-ray radiation to the tissue that lines a body cavity.

SUMMARY

An x-ray brachytherapy system and method is provided for applying x-rays to a treatment region in a patient's anatomy. In one embodiment, the system includes a catheter assembly, one or more flexible probe assemblies, and a power supply means. The catheter assembly includes one or more inflatable elements for positioning and/or stabilizing a catheter at a desired location. Each flexible probe assembly has an x-ray generator assembly coupled to an end of a flexible probe. The x-ray generator assembly includes a miniaturized x-ray source, which may be an optically activated x-ray source.

In one embodiment, the catheter assembly includes a catheter body member, and one or more inflatable elements coupled to points along the body member. One or more of the inflatable elements may be inflatable balloons, for example. The treatment region may be an interior surface of a body cavity, by way of example, or may be an exterior surface of an anatomical region that is exposed to x-rays, e.g. to receive skin treatment. When in an inflated state, each inflatable element can be used to firmly position the catheter body member within the body cavity or with respect to the anatomical region being treated.

In one embodiment, the catheter body member extends from a proximal end to a distal end, and defines one or more interior channels therewithin. Each flexible probe assembly is slidably positionable within at least one of these interior channels in the catheter body member. The flexible probe assembly includes a transmission path, which is adapted to transmit an activating energy (for example optical energy such as light) incident on a proximal end of the transmission path onto a distal end thereof. In one embodiment, the transmission path is an optical delivery structure, for example a fiber optical cable, and the x-ray generator assembly is coupled to the distal end of the transmission path.

In one embodiment, the x-ray generator assembly includes a substantially rigid, evacuated capsule, which encloses a miniaturized x-ray source. The x-ray source includes an electron source and a target element. The electron source emits electrons in response to the activating energy transmitted through the transmission path and directed to the electron source. The power supply means is coupled to the flexible probe assembly and the x-ray generator assembly, and provides an accelerating voltage between the electron source and the target element so as to establish an accelerating electric field which acts to accelerate electrons emitted from the electron source toward the target element. The target element, which includes at least one x-ray emissive material, emits x-rays when struck by the accelerated electrons.

In operation, when treating an interior surface of a body cavity, the catheter can be inserted through a body passageway (e.g. the urethra, by way of example) and into a body cavity, in such a way that the distal end of the catheter assembly is positioned near or within a body cavity (e.g. the bladder, as just one example), and the proximal end of the catheter remains external to the body. When treating an exterior body surface, the catheter may be attached at or near the body surface, for example in order to deliver radiation for skin treatment. Each flexible probe assembly can be inserted through at least one interior channel of the catheter so as to position the x-ray generator assembly, attached to its distal end, at predetermined locations inside the body cavity. In response to the activating energy delivered by the transmission path, the x-ray generator assembly provides a therapeutic dose of x-rays to the tissue lining the body cavity. Preferably, the x-ray generator assembly can provide a uniform or a specially contoured dose of x-rays.

In one embodiment, the electron source includes a laser-heated thermionic cathode. In this embodiment, the transmission path within the flexible probe assembly is a fiber optic cable. The fiber optic cable transmits optical radiation, such as light from a laser, from a proximal end of the cable onto a distal end of the cable, and the thermionic cathode is heated by the optical radiation to cause thermionic emission of electrons. Alternatively, other types of electron sources such as photocathodes may be used.

In one embodiment, a variable thickness, x-ray transmissive shield is used, in order to shape the spatial distribution of the x-rays into a desired or predetermined dose distribution. In this embodiment, the flux of the x-rays generated by the x-ray generator assembly is dependent in part upon the thickness of the variable transmission shield, as measured along an axis extending from the target element and passing through the target element. A selective restriction in thickness of the variable transmission shield can be used to generate spatially variable x-ray dose distributions.

According to another embodiment, the catheter further comprises one or more interior channels or passageways. Each interior channel extends from a point at or near the proximal end of the catheter to a point at or near the distal end of the catheter. The interior channel or passageway may be in communication with an interior region of an inflatable element or inflatable balloon, and establish a fluid flow path from the proximal end of the catheter to the interior region. The interior channel can thus functions as a fluid passageway for a fluid, so that the fluid may be carried from outside the catheter to the interior of inflatable element or balloon. The fluid passageway can provide a return path for the fluid, so that the fluid returns to the proximal portion of the catheter, after circulating through the interior of the balloon.

The fluid may be used to inflate and deflate the inflatable element or balloon, so that inflation and deflation of the balloon may be controlled from the proximal end of the catheter. In this case, an inflation device known in the art (including but not limited to a pump) may be coupled to the interior passageway, to control the inflation and deflation of the balloon, and to maintain a pressure within the balloon that is necessary to maintain the desired size and shape of the balloon.

In some embodiments, a cooling fluid may also be circulated in and out of the fluid passageway and through the interior of the balloon. The cooling fluid serves to carry heat away from the x-ray emitting tip of the probe, thereby dissipating excess heat that may deleteriously affect the operation of the x-ray brachytherapy system. The cooling fluid may be one of a number of cooling fluids known in the art, including but not limited to helium, or water, or fluorine, by way of example.

In another embodiment, the fluid that is circulated may be a heating fluid that is used to heat the tissue being treated, in order to improve the receptivity of the tissue to incident x-ray radiation. In yet another embodiment, the fluid may be used to control the radiation dose absorption and the radiation emission profile.

In one embodiment, the catheter may have one or more position controllers, for precise position control of the catheter assembly and/or the flexible probe assemblies. In one embodiment, the catheter may have one or more radiation dose controllers, for controlling the radiation dose delivered by the probe. In one embodiment, the catheter assembly and the flexible probe assembly may have a combined or integrated control system. In one embodiment, the integrated control system may include a controllable power supply, an optical driver, a control element for the pressure of the catheter and/or an inflation control system for the inflatable elements in the catheter, a probe position controller, a treatment planning system, and one or more interfaces to other diagnostic systems such as image data transfer protocols. The integrated control system can be equipped to operate one x-ray source at a time, or to operate multiple sources in parallel with different parameters, if necessary.

In one embodiment, the catheter assembly has a double-wall (or multi-wall) structure, including two or more tubes that may be concentrically disposed relative to one another. In this embodiment, the catheter may include: 1) a catheter body member that defines one or more interior channels; 2) an x-ray absorption control layer surrounding the body member; 3) at least one inner tube enclosing the catheter body member and the absorption control layer; 4) one or more inflatable elements coupled to the inner tube; and 5) at least one outer tube having a diameter greater than the inner tube. In one embodiment, the absorption control layer may be formed of at least partially x-ray absorptive material. The inner tube may be inflated to different pressures, using the inflatable elements. In this way, x-ray absorption may be controlled by controlling the inflation pressure exerted by the inflation elements on the inner tube. A fluid other than air may also be used to control the x-ray absorption.

BRIEF DESCRIPTION OF THE DRAWINGS

In FIG. 8A, the inflatable elements are shown in an inflated state. In FIG. 8B, the inflatable elements are shown in a deflated state.

DETAILED DESCRIPTION

A relatively small, electron-beam activated, low power x-ray brachytherapy apparatus can be fully implanted or partially inserted into an internal anatomical region of a patient, such as a body cavity. The brachytherapy apparatus can also be directly attached adjacent to a treatment region that is at or near the surface of the patient's body and that is to be exposed to x-ray radiation, for example for skin treatment. A catheter assembly including one or more x-ray probes and one or more inflatable elements (e.g. inflatable balloons) enables the delivery by a miniaturized x-ray source of a desired dose of x-ray radiation to a desired location, over selected exposure times. The desired location may be, for example, the interior surface of the body cavity, or the exterior surface of a treatment region in the patient's anatomy. The catheter assembly can be localized, for example by being affixed firmly to the treatment region, in order to properly direct x-rays to the right location.

Generally, the x-ray brachytherapy apparatus includes a miniaturized, electron-beam (e-beam) activated x-ray source, which operates at relatively low voltages, i.e. in the range of approximately 10 kV to 90 kV, and relatively small electron beam currents, i.e. in the range of approximately 1 nA to 100 μA. At those operating voltages and currents, the x-ray output is relatively low. The apparatus may be made quite small, and may be adapted for implantation in medical therapeutic applications. In view of the low-level x-ray output, adequate tissue penetration and cumulative dosage may be attained by locating the x-ray source within or adjacent to the region to be irradiated. Thus, the x-rays are emitted from a well-defined, small source located within or adjacent to the region to be irradiated. In one embodiment, a low dose-rate of x-rays may be applied to any part of a tumor, either continually or periodically.

Figure 1:
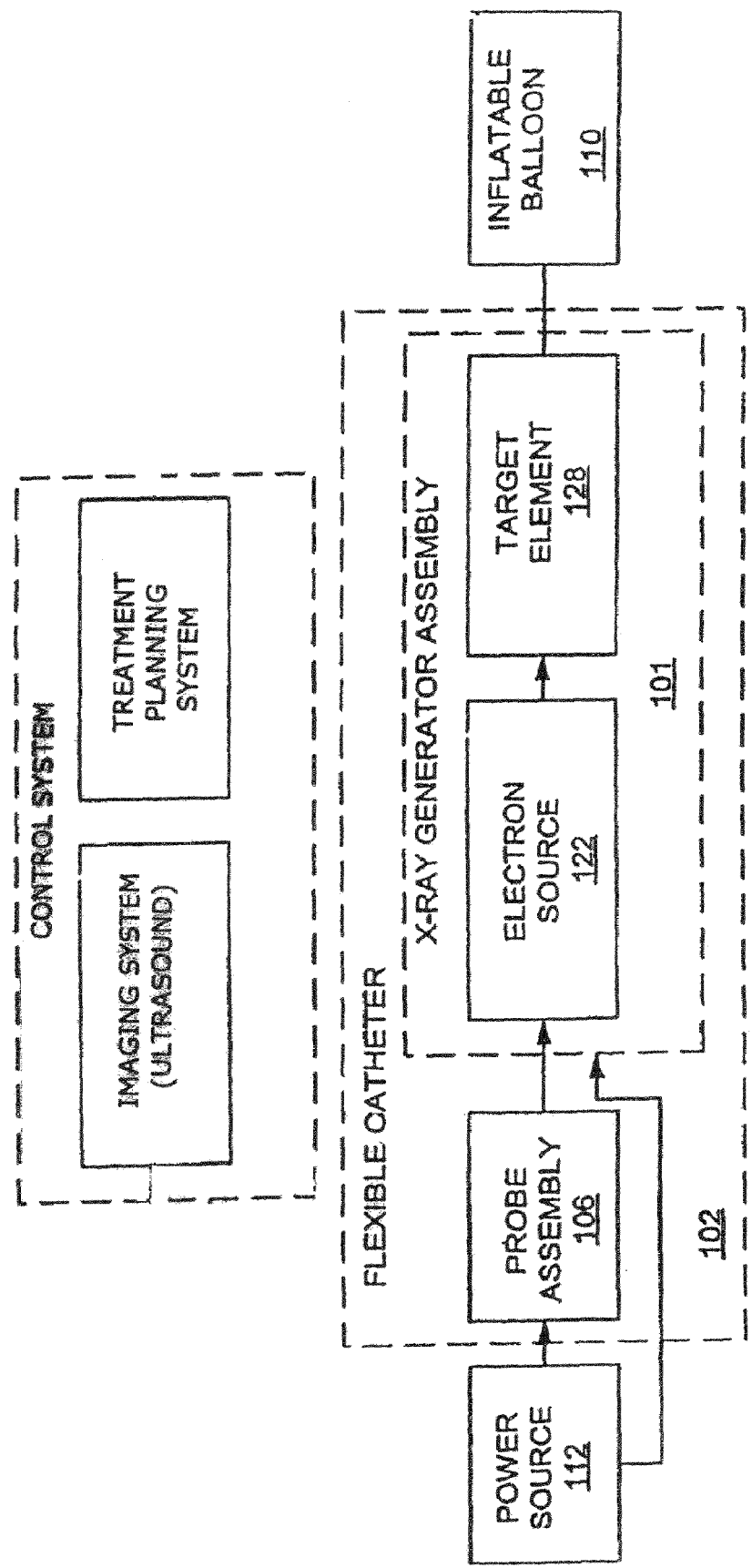
FIG. 1 is a schematic block diagram of an overview of an x-ray brachytherapy system, constructed in accordance with one embodiment.

FIG. 1 is a schematic block diagram of an overview of an x-ray brachytherapy apparatus 100, constructed in accordance with one embodiment. The apparatus 100 includes a catheter assembly 102, which encloses a flexible probe assembly 106 and an x-ray generator assembly 101. In the illustrated embodiment, the catheter assembly 102 is substantially flexible. The x-ray generator assembly 101 is coupled to the distal end of the flexible probe assembly 106.

The apparatus 100 also includes one or more inflatable elements 110, and a power source 112. One or more of the inflatable elements 110 may, for example, be an inflatable balloon.

Figure 9:
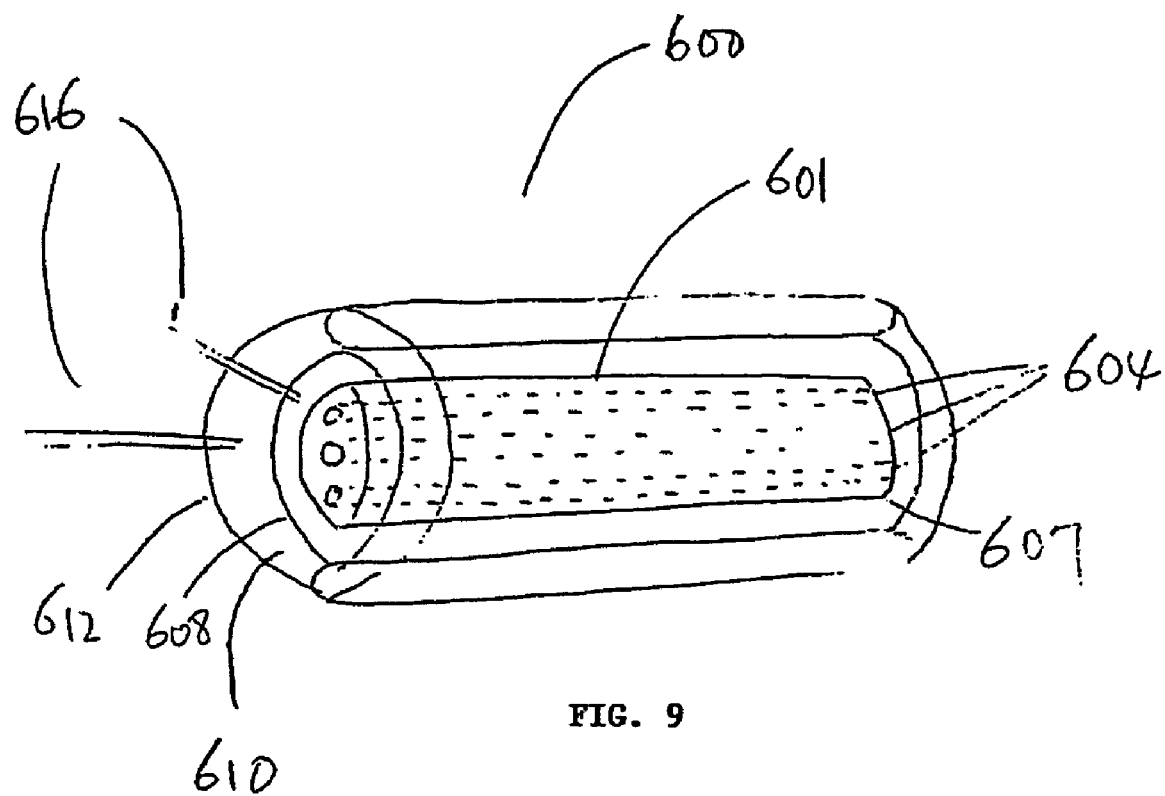
FIG. 9 illustrates a catheter assembly having 1) a catheter body member; 2) an x-ray absorption control layer surrounding the body member, the control layer made of at least partially x-ray absorptive material; 3) at least one inner tube; 4) at least one hollow tube having a diameter greater than the inner tube and concentrically disposed with respect to the inner tube; and 5) one or more inflatable elements coupled to the inner tube.

The catheter assembly 102 may be flexible or rigid, and as shown in the exemplary embodiment 600 of FIG. 9, may include a catheter body member 601 extending from one end to another, a balloon assembly 110 including one inner tube 608 enclosing the body member, and an outer tube 609 having a diameter greater than the inner tube. The catheter body member 601 may extend along a central axis, and may define one or more interior channels 604 along the central axis. The inflatable balloon 110 is affixed to, and extends from, the distal end of the catheter body member 601.

In one embodiment, the catheter body member 601 may be inserted through a body passageway, so that the distal end of the catheter, together with an inflatable balloon 110, is positioned near or within a body cavity of a patient, and the proximal end of the catheter remains external to the patient's body. The inflatable balloon 110 can be inflated from within an interior region of the body cavity, so as to define a predetermined surface contour disposed about the interior region. The flexible probe assembly 106 can be inserted through the interior channel of the catheter assembly 102, in such a way as to position the x-ray generator assembly 101 at a predetermined location inside the body member 601. When activated, the x-ray generator assembly 101 can provide a uniform or a specially contoured dose of x-rays to the interior surface of the body cavity.

Alternatively, in embodiments in which the treatment region to be exposed to therapeutic radiation is located at or near the surface of the patient's body, the catheter can be localized at the treatment region, so that the radiation can be directed to the right locations. In these embodiments, the inflatable elements can be inflated in order to affix the catheter firmly to the treatment region.

The power source 112 is coupled to the probe assembly 106 and the x-ray generator assembly 101. The power source 112 provides an accelerating voltage between the electron source 122 and the target element 128, so that an accelerating electric field accelerates the electrons emitted from the electron source 122 toward the target element 128. X-rays emitted when the accelerated electrons strike the target element 128.

Figure 2:
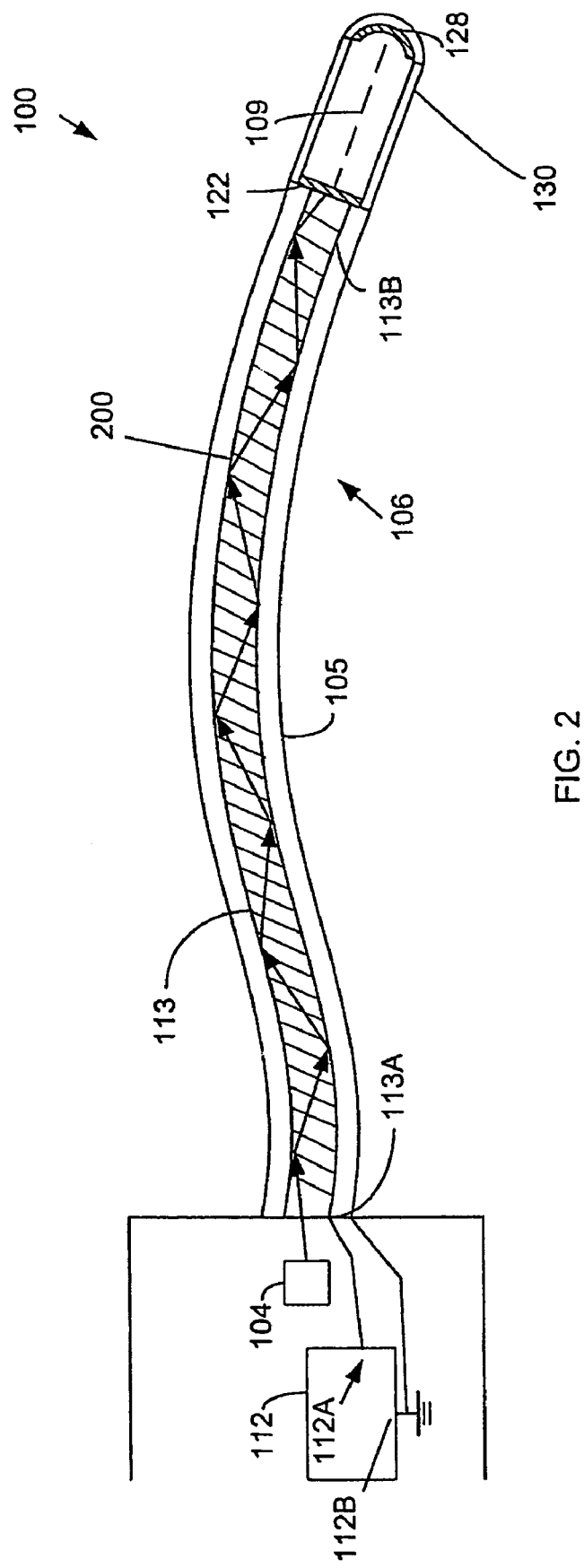
FIG. 2 is a diagrammatic view of a flexible probe assembly and an x-ray generator assembly, constructed in accordance with one embodiment.
Figure 3:
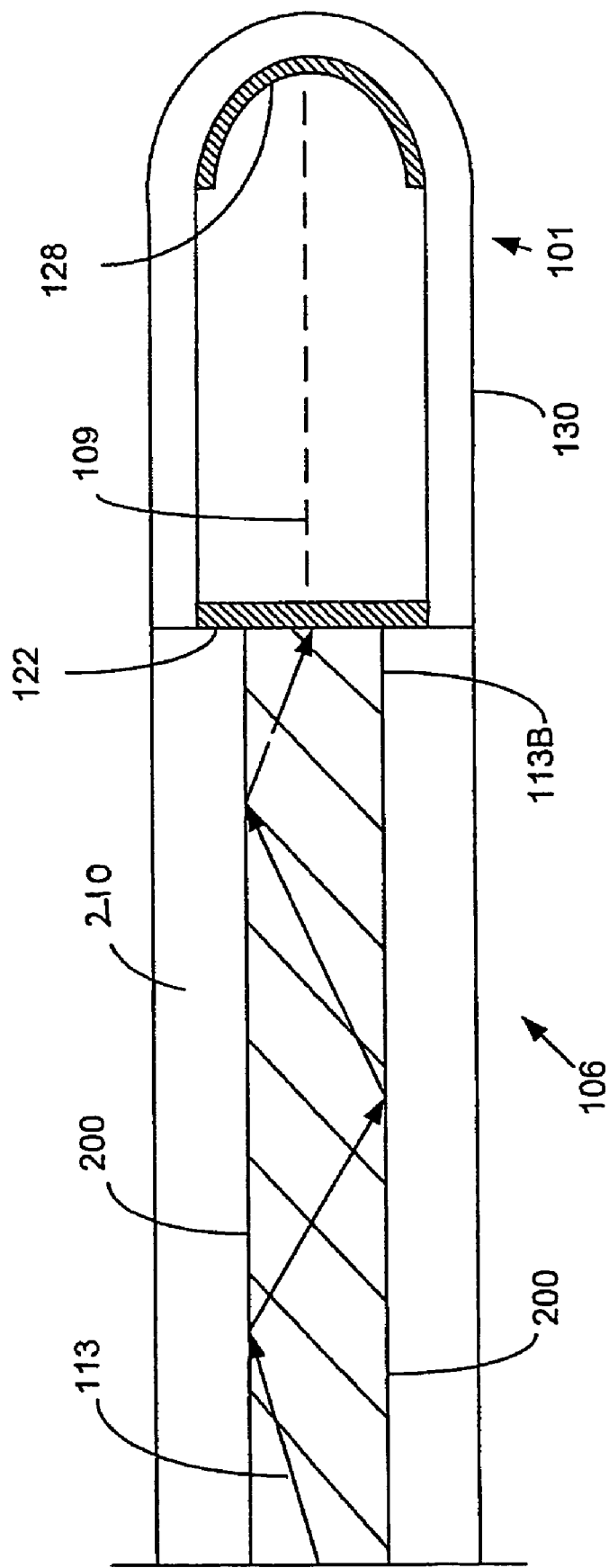
FIG. 3 is an enlarged diagrammatic view of the flexible probe assembly and the x-ray generator assembly.
Figure 4:
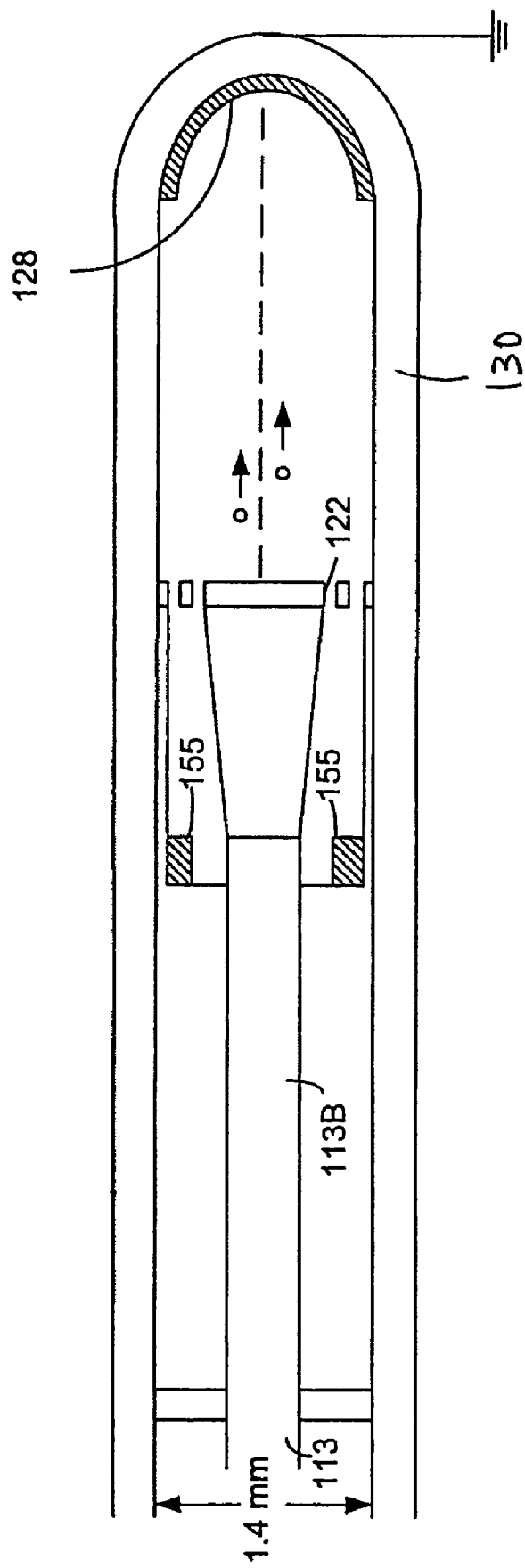
FIG. 4 is an enlarged view of one end of an x-ray generator assembly.

FIGS. 2, 3, and 4 illustrate an embodiment in which the electron source 122 is a thermionic cathode that is heated by optical radiation. Referring to FIG. 2, the x-ray brachytherapy apparatus 100 includes an optical source 104, a probe assembly 106, and an x-ray generator assembly 101. In the illustrated embodiment, the optical source 104 is a laser that generates a beam of laser light. The laser 104 may be a diode laser, by way of example; however, other lasers known in the art may be used, such as a Nd:YAG laser, a Nd:YVO$_4$ laser, or a molecular laser.

In alternative embodiments, other sources of high intensity light, preferably having a compact size, may be used. These sources of high intensity light may include, but are not limited to: LEDs (light emitting diodes); OLEDs (organic light emitting diodes); and SLEDs (superluminescent light emitting diodes). As known, OLEDs are made by placing a series of organic thin films between conductors, and are configured to emit a bright light when an electrical current is applied thereto. As known, SLEDs emit light by amplified spontaneous emission, with a narrower spectral width compared to conventional LEDs. Light emission in SLEDs is based on stimulated emission with amplification, by analogy to lasers, but without a built-in optical feedback mechanism necessary in order for the stimulated emission to achieve lasing. The advantages of SLDs over conventional LEDs include higher coupled power, narrower spectral width, and greater bandwidth.

The x-ray generator assembly 101 includes a target element 128, and an electron source 122. The target element 128 includes means for emitting therapeutic radiation in response to incident accelerated electrons, for example includes x-ray emissive material that is described in more detail below in conjunction with FIGS. 3 and 4. The probe assembly 106 includes a transmission path adapted to transmit an activating energy incident on a proximal end of the path onto a distal end of the path. In the embodiment illustrated in FIG. 3, the transmission path is an optical delivery structure 113, such as a fiber optic cable 113. The optical delivery-structure 113 directs a beam of laser radiation generated by the optical source 104 onto the thermionic cathode 122. The laser beam heats the thermionic cathode 122, so as to cause thermionic emission of electrons.

The electron source 122 generates an electron beam along a beam path 109. The target element 128 is positioned in the beam path 109. The x-ray brachytherapy apparatus 100 also includes means for providing an accelerating voltage between the electron source 122 and the target element 128, for example a power source 112. In the illustrated embodiment, the power source 112 is a high voltage power supply. As shown in FIG. 2, the probe assembly 106 couples the laser source 104 and the high voltage power supply 112 to the x-ray generator assembly 101.

FIG. 3 provides an overall view of the x-ray brachytherapy apparatus 100, whereas FIG. 4 provides a more detailed, enlarged view of: 1) the x-ray generator assembly 101, and 2) the distal end of the probe assembly 106. Referring to both FIGS. 3 and 4, the probe assembly 106 includes an optical delivery structure 113 having a proximal end 113A and a distal end 113B. In the illustrated embodiment, the distal end 113B of the optical delivery structure 113 is affixed to the x-ray generator assembly 101. In one embodiment, the optical delivery structure 113 is a flexible fiber optic cable, extending from the proximal end 113A to the distal end 113B. The probe assembly 106 may include a flexible metal sheath 105. The fiber optic cable 113 preferably includes an electrically conductive outer surface 200. For example, the outer surface of the fiber optic cable 113 may be made conductive by applying an electrically conductive coating. The electrically conductive outer surface 200 of the fiber optic cable 113 provides a connection to the thermionic cathode 122 from the high voltage power supply 112. In this embodiment, the x-ray generator assembly 101 also has an electrically conductive outer surface.

In one embodiment, both the flexible metallic sheath 105 and the outer conductive surface of the x-ray generator assembly 101 are set at ground potential, in order to reduce the shock hazard of the device. The flexible sheath 105 couples a ground return from the target element 128 to the high voltage power supply 112, thereby establishing a high voltage field between the thermionic cathode 122 and the target element 128. In an exemplary embodiment, the fiber optic cable 113 may have a diameter of about 200 microns, and the flexible metallic sheath 105 may have a diameter of about 1.4 mm. A layer 210 of dielectric material may provide insulation between the outer surface of the fiber optic cable 113 and the inner surface of the metallic sheath 105.

The x-ray generator assembly 101, which in exemplary embodiments may be about 0.5 to about 2 cm in length, extends from the distal end of the probe assembly 106, and includes a shell or capsule 130 which encloses the electron source 122 and the target element 128. In other embodiments, the x-ray generator assembly 101 may have different sizes. According to one embodiment, the capsule 130 is rigid in nature and generally cylindrical in shape. In this embodiment, the cylindrical capsule 130 enclosing the other elements of the x-ray generator assembly 101 can be considered to provide a substantially rigid housing for the electron source 122 and the target element 128. In this embodiment, the electron source 122 and the target element 128 are disposed within the capsule 130, with the electron source 122 disposed at a proximal end of the capsule 130, and the target element 128 disposed at a distal end of the capsule 130. The electron source 122 is a thermionic cathode 122 having an electron emissive surface.

The capsule 130 defines a substantially evacuated interior region extending along the beam axis 109, between the electron source 122 at the proximal end of the capsule 130 and the target element 128 at the distal end of the capsule 130. The inner surface of the x-ray generator assembly 101 is lined with an electrical insulator or semiconductor, while the external surface of the assembly 101 is electrically conductive, as mentioned earlier. A low secondary emission, controlled sheet resistance semiconducting film may be applied to the inner surface of the x-ray generator assembly 101, in order to maximize the breakdown voltage of the system. In one embodiment, the x-ray generator assembly 101 is hermetically sealed to the end of the probe assembly 106, and evacuated.

In the embodiments illustrated in FIGS. 3 and 4, the power supply 112 has a first terminal 112A and a second terminal 112B, and has drive means for establishing an output voltage between the first terminal 112A and the second terminal 112B. In one form, the power supply 112 may be electrically coupled to the x-ray generator assembly 101 by way of the first and second terminals. In the embodiment illustrated in FIGS. 3 and 4, the first terminal 112A of the power supply 112 is electrically coupled to the electron emissive surface of the thermionic cathode 122, and the second terminal 112B is electrically coupled to the target element 128. The high voltage power supply 112 provides a high potential difference across the conductive outer surface 200 of the fiber optic cable 113, and the metallic sheath 105, to establish an acceleration potential difference between the thermionic cathode 122 and the grounded target element 128.

In this way, electrons emitted from the thermionic cathode 122 are accelerated toward the target element 128, and an electron beam is generated. The electron beam is preferably thin (e.g. 1 mm or less in diameter), and is established along a beam path 109 along a nominally straight reference axis that extends to the target element 128. The target element 128 is positioned in the beam path 109. In one embodiment, the distance from the electron source 122 to the target element 128 is preferably less than 2 mm.

The high voltage power supply 112 preferably satisfies three criteria: 1) small in size; 2) high efficiency, so as to enable the use of battery power; and 3) independently variable x-ray tube voltage and current, so as to enable the unit to be programmed for specific applications. Preferably, the power supply 112 includes selectively operable control means, including means for selectively controlling the amplitude of the output voltage and the amplitude of the beam generator current. A high-frequency, switch-mode power converter is preferably used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of an exemplary power supply suitable for use as the power supply 112 is provided, for example, in the '900 patent and the '658 patent.

The target element 128 is preferably spaced apart from and opposite the electron emissive surface of the thermionic cathode 122, and has at least one x-ray emissive material adapted to emit therapeutic x-radiation in response to incident accelerated electrons from the electron emissive surface of the thermionic cathode 122. In one embodiment, the target element 128 is a small beryllium (Be) substrate, coated on the side exposed to the incident electron beam with a thin film or layer of a high-Z, x-ray emissive element, such as tungsten (W), uranium (U) or gold (Au). By way of example, when the electrons are accelerated to 30 keV-, a 2 micron thick gold layer absorbs substantially all of the incident electrons, while transmitting approximately 95% of any 30 keV-, 88% of any 20 keV-, and 83% of any 10 keV-x-rays generated in that layer. In this embodiment, the beryllium substrate is 0.5 mm thick. With this configuration, 95% of the x-rays generated in directions normal to and toward the beryllium substrate, and having passed through the gold layer, are then transmitted through the beryllium substrate and outward at the distal end of the probe assembly 106.

In some embodiments, the target element 128 may include a multiple layer film, where the differing layers may have different emission characteristics. By way of example, the first layer may have an emission versus energy peak at a relatively low energy, and the second underlying layer may have an emission versus energy peak at a relatively high energy. In these embodiments, a low energy electron beam may be used to generate x-rays in the first layer, to achieve a first radiation characteristic, and high energy electrons may be used to penetrate through to the underlying layer, to achieve a second radiation characteristic. As an example, a 0.5 mm wide electron beam may be emitted at the cathode and accelerated to 30 keV, with 0.1 eV transverse electron energies, and may arrive at the target element 128, with a beam diameter of less than 1 mm at the target element 128. X-rays are generated in the target element 128 in accordance with pre-selected beam voltage, current, and target element composition. The x-rays thus generated pass through the beryllium substrate with minimized loss in energy.

As an alternative to beryllium, the target substrate may be made of carbon, ceramic such as boron nitride, or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution. In other embodiments, the target may be a solid, high-Z material, with x-rays being emitted in an annular beam perpendicular to the tube axis.

FIG. 4 illustrates an electron source 122 that includes a laser-heated thermionic cathode 122. The thermionic cathode 122 has an electron emissive surface, and is typically formed of a metallic material. Suitable metallic materials forming the cathode 122 may include tungsten, thoriated tungsten, other tungsten alloys, thoriated rhenium, and tantalum. The cathode disc can be held in place by means of swage of the end or by laser welding. In one embodiment, the cathode 122 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 122 may also be an oxide coated cathode, where a coating of the mixed oxides of barium and strontium, by way of example, may be applied to a metallic base, such as nickel or a nickel alloy. The metallic base may be made of other materials, including Group VI metals such as tungsten.

Getters 155 may be positioned within the housing 130. The getters 155 aid in creating and maintaining a vacuum condition of high quality. Typically, getters have an activation temperature, after which they will react with stray gas molecules in the vacuum. It is desirable that the getters used have an activation temperature that is not so high as to damage the x-ray device, when heated to the activation temperature.

The fiber optic cable 113 is adapted to transmit laser radiation, generated by the laser source 104 (shown in FIG. 3) and incident on the proximal end 113A of the fiber optic cable 113, to the distal end 113B of the fiber optic cable 113. The fiber optic cable 113 is also adapted to deliver a beam of the transmitted laser radiation to impinge upon the electron-emissive surface of the thermionic cathode 122. The beam of laser radiation should have a power level sufficient to heat at least a portion of the electron-emissive surface to an electron emitting temperature, so as to cause thermionic emission of electrons from the surface.

The operation of the probe assembly 106 and the x-ray generator assembly 101 typically includes the following steps. A laser beam shining down the fiber optic cable 113 impinges upon the surface of the thermionic cathode 122, and rapidly heats the surface to an electron emitting temperature, below the melting point of the metallic cathode 122. When the surface of the thermionic cathode 122 reaches an electron emitting temperature, electrons are thermionically emitted from the surface. The high voltage field between the cathode 122 and the target element 128 (shown in FIGS. 3 and 4) accelerates these electrons, thereby forcing them to strike the surface of the target element 128, so that x-rays are generated. In one embodiment, a Nd:YAG laser was coupled into a $SiO_2$ optical fiber having a diameter of 400 microns. A 20 kV power supply was used, and a thermionic cathode made of tungsten was used. Only a few watts of power was needed to generate over 100 □A of electron current. In another example, an infrared diode laser was used to achieve about 100 □A of electron current with only 180 mW of power.

Figure 5:
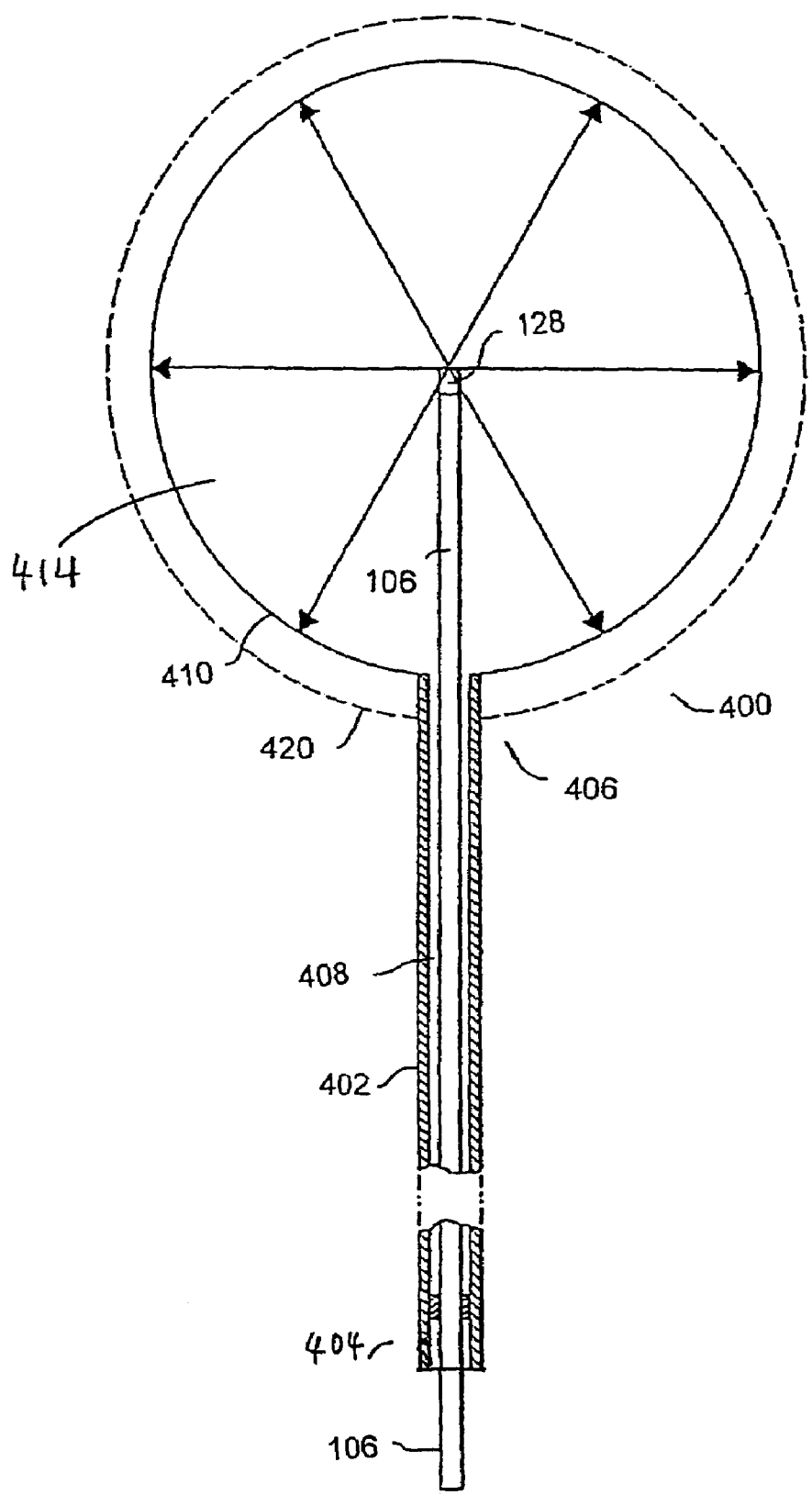
FIG. 5 illustrates an x-ray brachytherapy system including a flexible catheter, a flexible probe assembly, an inflatable balloon in an inflated state, and an x-ray generator assembly disposed substantially at the center of the inflated balloon.

FIG. 5 shows a catheter assembly 400, including a flexible catheter body member 402, and an inflatable element 410 disposed at or near a distal end of the catheter body 402. In the illustrated embodiment, the flexible catheter body 402 extends along a central axis, and has a proximal end 404 and a distal end 406. Also, in this embodiment the inflatable element 410 is a balloon, and the catheter body 402 has an interior channel 408 extending along the central axis. The inflatable balloon 410 is affixed to the outside of the distal end 406 of the catheter 402. In FIG. 5, the balloon 410 is shown in its inflated state. Although in FIG. 5, the balloon 410 is shown as having a substantially spherical shape in its inflated state, in other embodiments the inflatable balloon can take on many different shapes when inflated. These shapes include, but are not limited to, spherical, elliptical, and cylindrical shapes, some or all of which can be used in treating anatomical regions such as the bladder or the colon.

The probe assembly 106 (previously described, in conjunction with FIGS. 2, 3, and 4) is slidably positionable within the interior channel 408, so that the distal end of the probe 106 can be positioned within the interior region of the balloon 410, when the balloon is inflated. In its inflated state, the balloon 410 defines a substantially spherical region 414, as shown in FIG. 5. In the illustrated embodiment, the target element 128 is substantially at the center of the spherical region 414 defined by the inflated balloon 410. Inflation and deflation of the balloon 410 can be controlled from the proximal end 404 of the probe 106, as described below.

In the embodiment illustrated in FIG. 5, in practice the balloon 410 is initially deflated, then folded and packed around the distal end 406 of the catheter 402. The distal end 406 of the catheter 402, with the deflated and folded balloon 410, is then inserted into the body of a patient, in such a manner that the distal end 406 is positioned within the body cavity to be treated. The proximal end 404 remains external to the patient during the entire procedure. After the distal end 406 has been inserted into the body cavity, the balloon 410 is inflated so that the body cavity becomes stretched into a spherical shape.

In many instances, when treating a body cavity with radiation therapy, it may be desirable to uniformly radiate the entire surface of the soft tissue lining the cavity, such that an isodose contour is coincident with the surface of the body cavity. An isodose contour is a surface in which the absorbed radiation energy is equal at every point on the surface. One method of uniformly radiating a body cavity, as disclosed in the '780 patent, is to first use a device such as an inelastic balloon to stretch the cavity into a substantially spherical shape, and then position an omnidirectional x-ray generating probe tip at the center of the cavity. With this configuration, an isodose contour can be established that is coincident with the surface of the body cavity.

In some embodiments, one of which is shown in FIG. 5, a surface of a body cavity is first conformed to a predetermined contour. FIG. 5 shows the balloon 410 as positioned within a body cavity 420 (shown in dotted lines). The body cavity 420 could be, by way of example, the bladder or the uterus. Initially the body cavity 420 defines a non-uniform shape, but inflating the balloon 410 stretches the lining of the cavity 420 into a substantially spherical in which the body cavity provides relatively little resistance to the inflation. Preferably, after inflation, substantially all of the exterior surface of the balloon 410 contacts the interior surface of the cavity 420. In other words, the balloon may be inflated so that it is in contact with the lining of the body cavity, and displaces that cavity to define a desired shape for that lining.

FIG. 5 also shows a channel 408 extending within the catheter 402 and in parallel with the probe assembly 106, establishing a gas flow path by which the balloon 410 can be inflated from outside the patient. In the illustrated embodiment, the probe 106 is inserted such that the target element 128 is positioned at the center of the balloon 410. Since the balloon 410 has stretched the cavity 420 into a spherical shape, the center of the balloon 410 is coincident with the center of the cavity 420. Accordingly, positioning target element 128 at the center of the inflated balloon 400 also centers the target element 128 within the body cavity 420. Once the target element 128 is centered, the electron source 122 may be activated to direct an electron beam so that the beam is incident on the target element 128. The result of the electron beam being incident on the target element 128 is the generation of x-ray radiation, with an isodose contour coincident with the spherical shape defined by the inflated balloon 410, and with the lining of the deformed body cavity 420. The flux density of the x-ray radiation decreases with distance from the x-ray source beyond the cavity lining, permitting treatment of the lining surface and diminishing effects in tissue beyond that lining.

Figure 6:
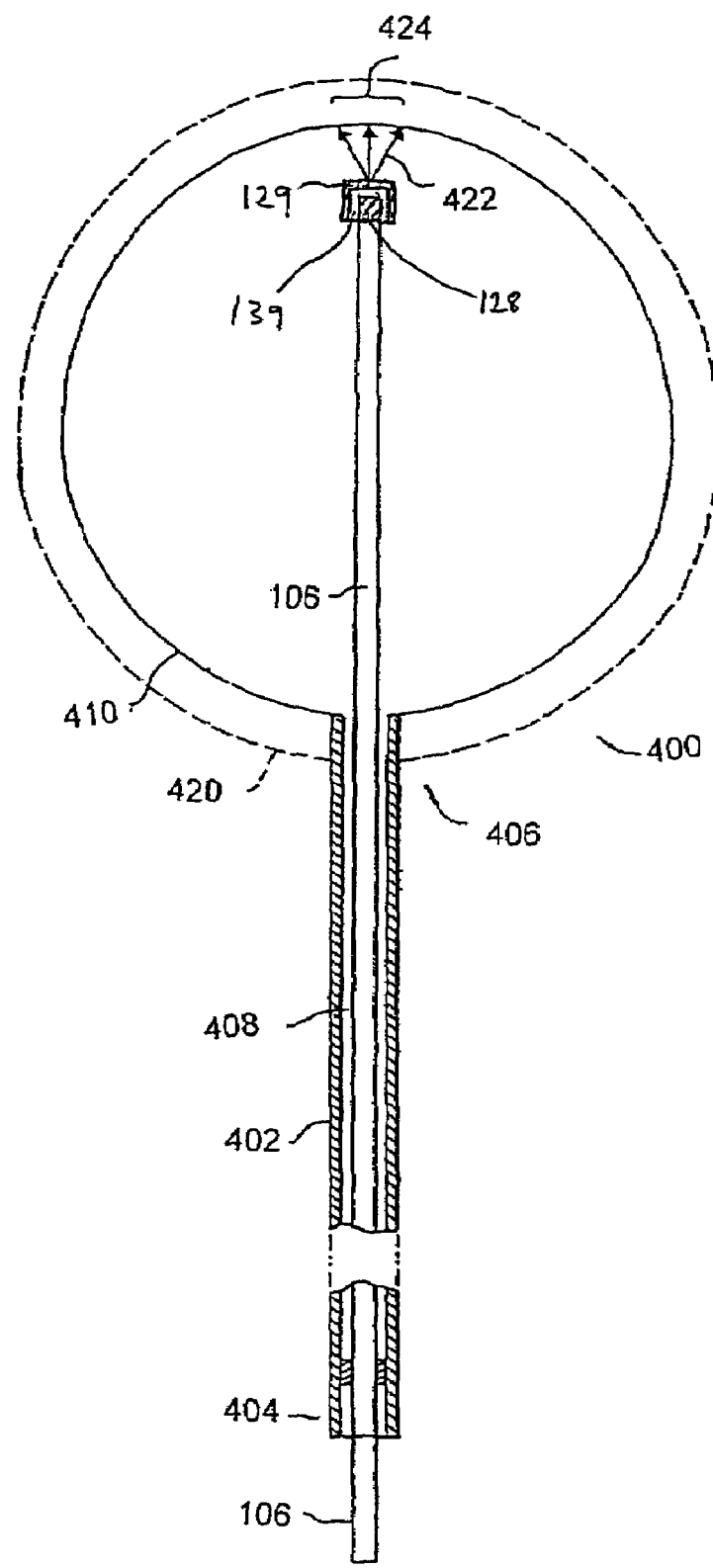
FIG. 6 shows an x-ray brachytherapy system as in FIG. 5 further including a variable thickness, x-ray transmissive shield for limiting the x-ray treatment to a specific section or region of a body cavity.

FIG. 6 shows another embodiment in which the x-ray treatment can be limited to a specific section or region of a body cavity, for example to a region containing tumorous tissue. In the embodiment shown in FIG. 6, a variable thickness, x-ray transmissive shield 129 (henceforth "variable transmission shield") is used, so as to shape the spatial distribution of the x-rays into a desired or predetermined dose distribution. The x-ray transmissive shield is sometimes referred to in the art as a "shadow mask."

In this embodiment, the electron source 122 generates an electron beam along a beam path disposed along a beam axis. The target element 128 has a surface positioned in the beam path, and is responsive to electrons from the electron beam that are incident on that surface to emit x-rays. A probe tip assembly 139 that is substantially x-ray transparent is provided at the distal end of the probe 106. The probe tip assembly 139 and associated control electronics (not shown) include elements for positioning the target element 128 in the beam path of the electron beam generated by the electron source 122. The probe tip assembly establishes a generally convex outer surface at the distal end of the probe assembly. A more detailed description of an exemplary probe tip assembly is provided in the '926 patent.

The variable transmission shield 129 is positioned on the outer surface of the probe tip assembly 139, and is adapted to control the position of the isodose surfaces of the x-rays emitted from the target and passing through the probe tip assembly 139. The variable transmission shield 129 is made from a material which is not completely x-ray transparent (i.e. is at least partially x-ray absorptive), such as heavy metals, by way of example. The x-ray flux from the x-ray generator assembly 101 is dependent in part upon the thickness of the variable transmission shield 129 along an axis extending from the target element 128 and passing through the target element 128. A selective restriction in thickness of the variable transmission shield 129 is used to generate spatially variable x-ray dose distributions.

In the exemplary embodiment illustrated in FIG. 6, the target element 128 is shielded by the variable transmission shield 129 in such a way that only those x-rays traveling in the direction of a forward solid angle, indicated in FIG. 6 by arrows 422, are emitted from the target element 128. In this way, only a specific, limited region within the body cavity 420, indicated in FIG. 6 by reference numeral 424, is radiated. It is understood, however, that the variable transmission shield 129 can be used to generate x-ray radiation fields having any type of desired configurations, including but not limited to, radiation fields in the shape of oblate or prolate ellipsoids, as described in detail in the '926 patent.

Figure 7:
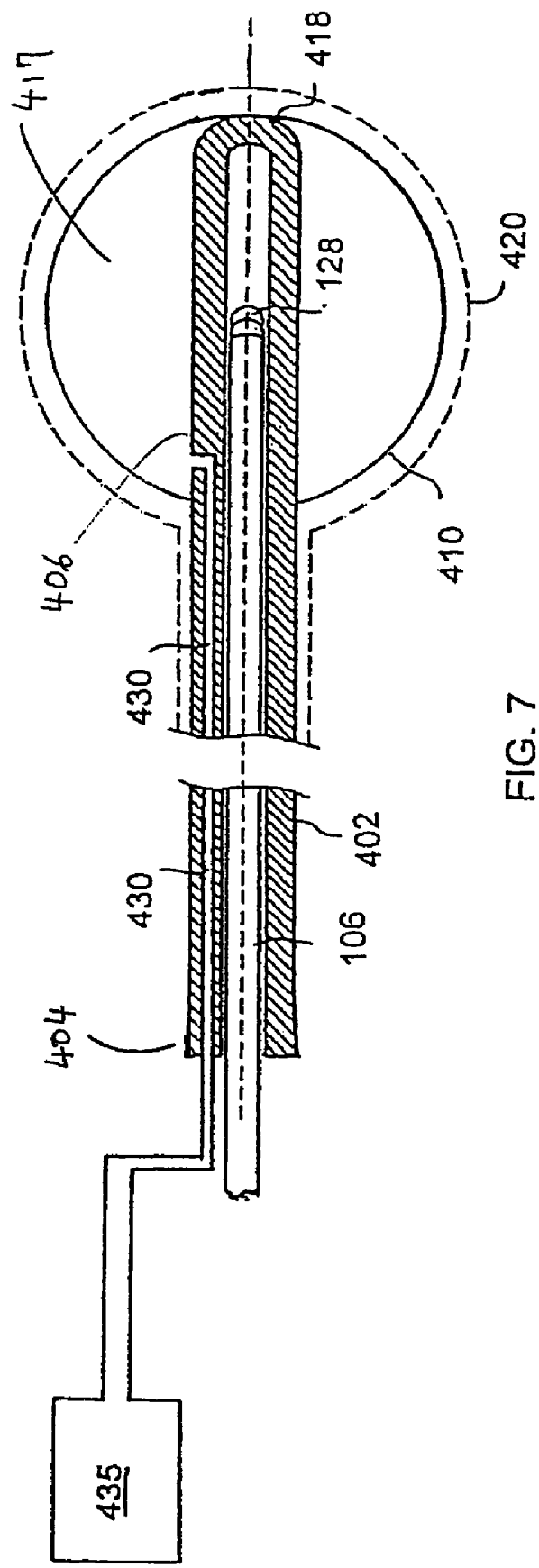
FIG. 7 is a sectional view of an x-ray brachytherapy system as in FIG. 5 in which the catheter comprises an interior channel extending from a point at or near the proximal end of the catheter to a point at or near the distal end of the catheter, and providing for a fluid passageway for a fluid used to inflate the balloon, and/or a cooling fluid for dissipating excess heat from the x-ray generator assembly.

In another embodiment, as illustrated in FIG. 7, the flexible catheter 402 comprises an interior passageway 430 extending from a point at or near its proximal end 404 to a point at or near its distal end 406. The interior passageway 430 is in communication with an interior region 417 of the balloon 410, and establishes a fluid flow path from the proximal end 404 of the catheter 402 to the interior region 417 of the balloon 410. The passageway 430 in the illustrated embodiment is thus a fluid passageway 430, allowing a fluid to be carried from outside the catheter 402 to the interior of the balloon 410. The fluid passageway 430 also provides a return path for the fluid, so that the fluid returns to the proximal portion 404 of the catheter 402, after circulating through the interior of the balloon 410.

The fluid may be a gas or a liquid that can bemused to inflate the balloon 410. In the embodiment illustrated in FIG. 7, the fluid is air that is used to inflate and deflate the balloon 410. In this embodiment, inflation and deflation of the balloon 410 may be controlled from the proximal end of the catheter 402, by coupling an inflation device 435 known in the art (including but not limited to a pump) to the fluid passageway 430, to control the inflation and deflation of the balloon 410, and to maintain an air pressure within the balloon 410 that is necessary to maintain the desired size and shape of the balloon 410. The inflation device 435 may be, but is not limited to, a pump.

In some embodiments, the fluid may be a cooling fluid that is circulated in and out of the fluid passageway 430 and through the interior of the balloon 410. The cooling fluid serves to carry heat away from the x-ray emitting tip of the probe, thereby dissipating excess heat that may deleteriously affect the operation of the x-ray brachytherapy system. The cooling fluid may be one of a number of cooling fluids known in the art, including but not limited to helium, or water, or fluorine, by way of example. A pump (not shown), coupled to the fluid passageway 430 through one or more fluid ports, may be used to circulate the cooling fluid.

In an alternate embodiment, the fluid may be a heating fluid. The heating fluid may be used to heat the tissue to an elevated temperature to make it more receptive to the desired impact of the applied x-ray radiation, thereby improving the therapeutic treatment.

In another embodiment, the fluid that fills up the inflatable elements or the fluid passageways in the rigid or flexible catheter may be used to modify the absorption of x-ray radiation by the tissue being treated. In other words, in some embodiments x-ray absorption can be controlled by using a fluid, rather by modifying the inflation pressure. In these embodiments, the fluid can act as a variable attenuator for the applied x-rays, controlling the absorption of x-rays by the tissue being treated, and equivalently, the x-ray emission profile. Examples of fluids that may be used for this purpose include, but are not limited to: air; water; and a solution of NaCl.

Figure 8A:
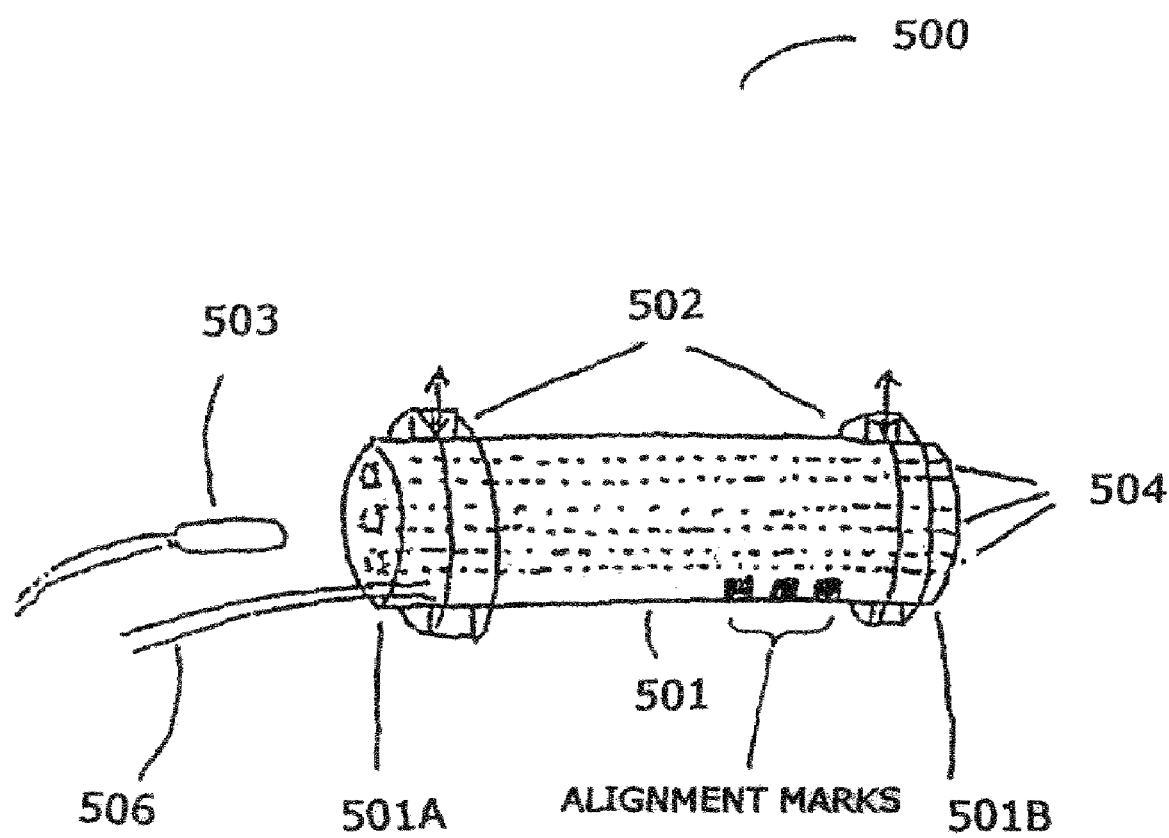
FIGS. 8A-8B provide a schematic view of a catheter for an x-ray brachytherapy system, where the catheter includes 1) a substantially rigid body member; 2) a plurality of inflatable elements that are adapted, when inflated from within a body cavity, to fixedly position the catheter with respect to a body cavity; and 3) a plurality of interior channels that are defined within the catheter so as to permit a plurality of flexible probes to be inserted in the interior channels of the catheter.
Figure 8B:
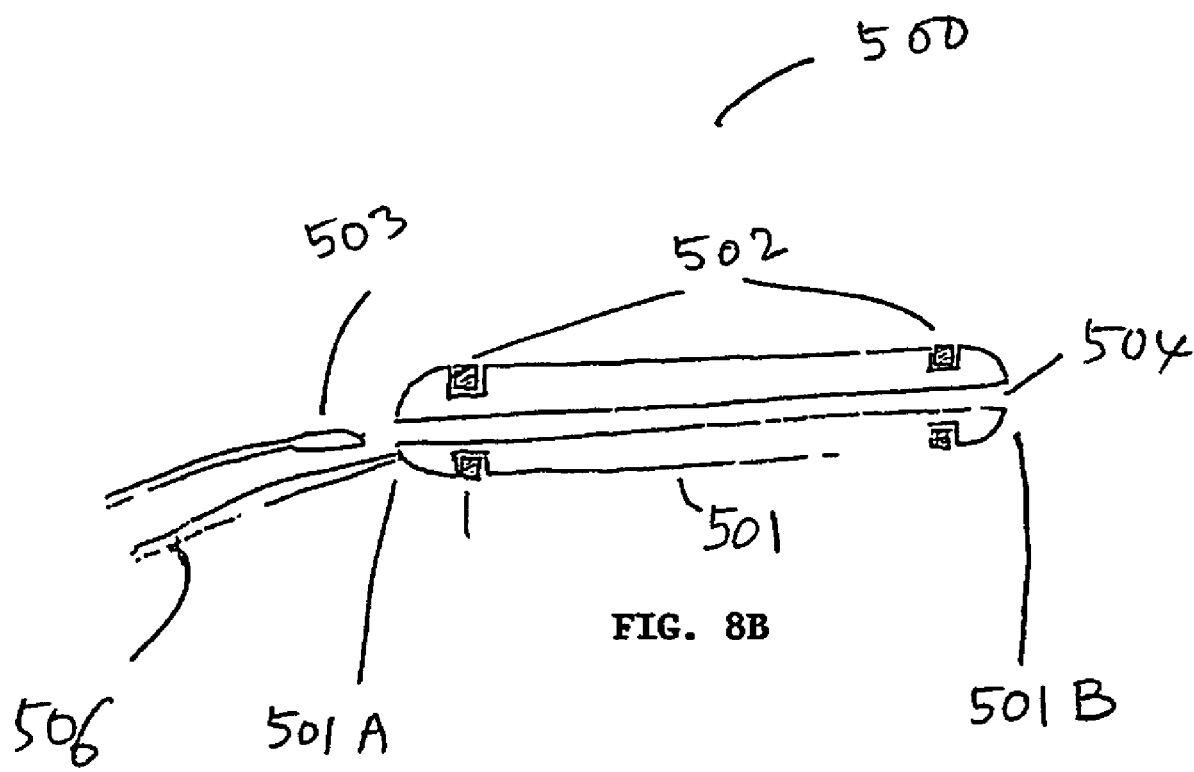

FIGS. 8A-8B provide a schematic view of an embodiment in which the catheter assembly includes a plurality of inflatable elements, and in which a plurality of interior channels are defined within the catheter so as to permit a plurality of flexible probes to be inserted in the interior channels of the catheter. In FIG. 8A, the inflatable elements are shown in their inflated states. In FIG. 8B, the inflatable elements are shown in their deflated states.

In the embodiment illustrated in FIG. 8A, a catheter assembly 500 includes a catheter body member 501 extending from a proximal end 501A to a distal end 501B, and one or more inflatable elements 502 affixed to the catheter body 501 at points along the body member 501. In one embodiment, the catheter body member 501 may be a substantially rigid member, shaped and configured to open up the body passageway through which the catheter is inserted. The catheter body member may have a substantially tubular or cylindrical configuration, or a substantially conical configuration. Alternatively, the catheter body member may have any other practical shape and configuration for opening up the body passageway. Alternatively, the catheter body member may be a substantially flexible member.

The inflatable element 502 may be a balloon, for example, and may be made of a substantially resilient material. Each inflatable element 502, when inflated, defines a predetermined surface contour (e.g. spherical, elliptical etc.). When inflated from within a body passageway or body cavity, the inflated elements 502 are adapted to firmly position the catheter within the body passageway or body cavity. In one embodiment, the inflatable elements 502, when inflated from within an interior region of a body cavity, define a predetermined surface contour disposed about the interior region. One or more of the inflatable elements may be inflatable balloons, for example. The one or more inflatable elements may be movably positioned inside the catheter at variable locations therealong. Alternatively, the inflatable elements may be fixedly positioned at predetermined positions.

The catheter body member 501 defines one or more interior channels 504. In the embodiment illustrated in FIG. 8, a plurality of interior channels are defined by the body member 501. Each interior channel 504 extends between points at or near the proximal end 501A of the rigid element 501, and points at or near the distal end 501B of the rigid element 501. A flexible probe 503 can be inserted through each interior channel 504, in such a way as to position a miniature x-ray generator assembly at one or more desired locations within the body passageway and/or body cavity.

In embodiments which include a plurality of x-ray probes positioned within respective interior channels, shielding may be included within the catheter body member 501. In these embodiments, one or more of the plurality of probes may be surrounded by one or more layers of x-ray absorptive shielding. Alternatively, x-ray shielding material could be included within each channel 504 defined within the catheter body member 501. By including shielding in this manner, overlaps between the radiation fields generated by each miniature x-ray source in each of the plurality of x-ray probes can be avoided or minimized.

The catheter assembly 500 further includes a passageway 506 in communication with the interior region of one or more of the inflatable elements 502. The passageway 506 allows a fluid, or other type of inflation control medium, to be carried from outside the catheter assembly 500 to the interior of one or more flexible elements 502. The control medium may be a gas (e.g. air) or a liquid or a fluid that can be used to inflate the inflatable elements 502. The inflation and deflation of the inflatable elements 502 may be controlled by coupling an inflation device (e.g. a fluid pump) to the passageway 506, e.g. to maintain a fluid pressure within each inflatable element at a level requisite for maintaining the desired size and shape of the inflatable elements 502.

Although a plurality of interior channels are shown in FIG. 8A, in some embodiments the catheter assembly 500 may have a single interior channel. Thus, the catheter assembly 500 can have one or multiple interior channels, so that one or multiple flexible probes can be inserted in the channels, at a time. In one embodiment, the flexible probes may be operated in parallel. In another embodiment, the flexible probes may be operated sequentially, one after another. In other embodiments, the flexible probes may be operated using a combination of parallel and sequential modes.

In one embodiment, the x-ray brachytherapy apparatus may have a rotatable mount (not shown), which allows rotational as well as translational motion of the x-ray generator assembly 101. In this embodiment, the rotatable mount may be pneumatically actuated, for example by one or more of the inflatable elements 502. In an embodiment in which a plurality of interior catheter channels and a plurality of flexible probes are provided, the rotatable mount can allow the radiation emission profile resulting from the cumulative effect of all x-ray sources to be smoothened out, by causing one or more x-ray sources to be rotated.

In an embodiment that includes multiple flexible probes, the multiprobe catheter assembly opens up, when one or more of the inflatable elements are inflated. When the multiprobe assembly opens up, the x-ray source can be placed closer to the border of the body cavity, in order to transmit a higher dose to the tissue lining the body cavity, and thereby cut down treatment time. In combination with the rotatable mount discussed above, this procedure can be helpful in order to provide a more homogeneous dose profile.

The x-ray brachytherapy apparatus may have one or more position controllers (not illustrated), for precise position control of the catheter assembly and/or the flexible probe assemblies. These control elements may use imaging or visualization techniques, including but not limited to ultrasonic imaging, x-ray imaging, and optical imaging, to determine the exact position of the catheter and/or the flexible probes.

In one embodiment, the body of the catheter may include one or more alignment marks, which can be contrasted using imaging systems (as discussed above), to check the proper position and orientation (i.e. both the translational and rotational coordinates) of the catheter assembly prior to delivering treatment to the target region of the patient's anatomy.

The x-ray brachytherapy apparatus may have one or more radiation dose controllers (not illustrated) for controlling the radiation dose delivered by the probe. The radiation dose controllers permit the total radiation dose, to which the patient has been exposed to, to be measured. In one embodiment, the radiation dose controllers permit the probe to be operated online.

In some embodiments, the x-ray brachytherapy apparatus may have an integrated control system (not illustrated) for controlling a plurality of features, or all of the features, relating to the operation of the x-ray brachytherapy apparatus. In one embodiment, the integrated control system includes one or more of the following: a) a controllable power supply for providing a controllable acceleration voltage between the electron source and the x-ray target element; b) an optical driver for activating and de-activating (i.e., turning on/off) the laser or other type of optical source; c) a pressure controller for controlling the pressure of the catheter and/or an inflation controller for controlling the inflation of the one or more inflation elements and/or one or more inner tubes of the catheter; d) a position controller for precisely controlling the position of the catheter assembly and/or the one or more flexible probe assemblies; e) a treatment planning system that controls the radiation dose delivered by the x-ray source, for example by determining the directions and intensities of the applied x-ray beams, and the durations of the x-ray beam exposure; and optionally f) one or more interfaces to other diagnostic systems, including but not limited to an interface to image data transfer and other standardized data protocols, and an interface to 2D- or 3D-patient data for treatment planning.

In an embodiment in which a plurality of x-ray probes are included within the x-ray brachytherapy apparatus, the integrated control system described above may be used to operate one x-ray source at a time, or if necessary may be used to operate a plurality of sources in parallel, simultaneously, as mentioned above. U.S. Pat. No. 6,556,651 ("the '651 patent"), entitled "Array of Miniature Radiation Sources," which is commonly owned by the assignee of the present application, discloses a system for delivering therapeutic radiation that includes a plurality of individually controllable therapeutic radiation sources. The radiation sources are selectively and moveably disposed along a selected axis or surface or volume, so as to form a one-dimensional or multi-dimensional array. U.S. Pat. No. 6,728,335 ("the '335 patent"), entitled "Controller for Array of Miniature Radiation Sources," which is commonly owned by the assignee of the present application, discloses a controller for selectively and independently controlling each of a plurality of therapeutic radiation sources. The controller disclosed in the '335 patent includes intensity control circuitry for controlling the intensity of the radiation generated by each source, as well as duration control circuitry for controlling the duration of the radiation generated by each source. Both the '651 patent and the '335 patent are hereby incorporated by reference in their entireties.

In some embodiments, the catheter assembly has a double-wall (or multi-wall) structure, and includes two or more tubes. In the embodiment illustrated in FIG. 9, a double-wall catheter 600 includes: 1) a substantially rigid, tubular body member 601, defining one or more interior channels 604 through which flexible probe assemblies can be positioned; 2) a layer 607 surrounding the catheter body member 601, the layer 607 being formed of at least partially x-ray absorptive material; 3) an inner tube 608, which provides the first wall of the double-wall catheter; 4) one or more inflatable elements 610 coupled to the inner tube 608 at points along the inner tube 608; 5) at least one outer tube 612 having a diameter greater than the inner tube 608, and providing the second wall of the double-wall catheter; 6) one or more passageways 616 for supplying control media to the absorption layer 607 and/or the inflatable element 610, to effect radiation control by means of pressure.

In an embodiment in which the fluid that fills one or more of the inflatable elements is used to control the radiation dose absorption and the radiation emission profile, each of the plurality of the inflatable elements may be positioned in relation to a corresponding individual x-ray source in such a way that each inflatable element can individually control the dose and radiation characteristics of the corresponding x-ray source.

In the illustrated embodiment, the inner tube 608 and the outer tube 612 are concentrically disposed relative to one another, providing the double-wall structure. Although in the illustrated embodiment, the outer tube 612 and the inner tube 608 are shown to be concentrically disposed with respect to one another, in other embodiments the inner and outer tubes may be disposed in a non-concentric configuration relative to one another. In one embodiment, more than two tubes may be provided in the catheter assembly. In this embodiment, catheter may include a plurality of interior passageways for supply of media (e.g. fluid, air, water etc.) to the inflatable elements coupled to the different tubes.

In the illustrated embodiment, the layer 607 is a controllable x-ray absorption layer, i.e. functions as a control element that controls the degree of absorption of the x-rays emitted by the x-ray generator assemblies. The inner tube 608 can be inflated to different pressures, without significantly affecting its outer dimensions. In this embodiment, x-ray absorption can be controlled by controlling the inflation pressure of the inner tube 608, i.e. by controlling the pressure to which the inner tube 608 is inflated. As discussed before, x-ray absorption can also be controlled by using a fluid, rather than by controlling the inflation pressure.

In one embodiment, instead of a single x-ray absorption layer 607, a plurality of x-ray absorption control elements may be provided. In this embodiment, the status of the different control elements may be controlled by providing different passageways, so that each chamber in the catheter can have an associated passageway for individual control of x-ray absorption. In this embodiment, the multiple inflatable elements may be related in position to the individual x-ray sources, so that their radiation dose and emission characteristics can be individually controlled.

Figure 10:
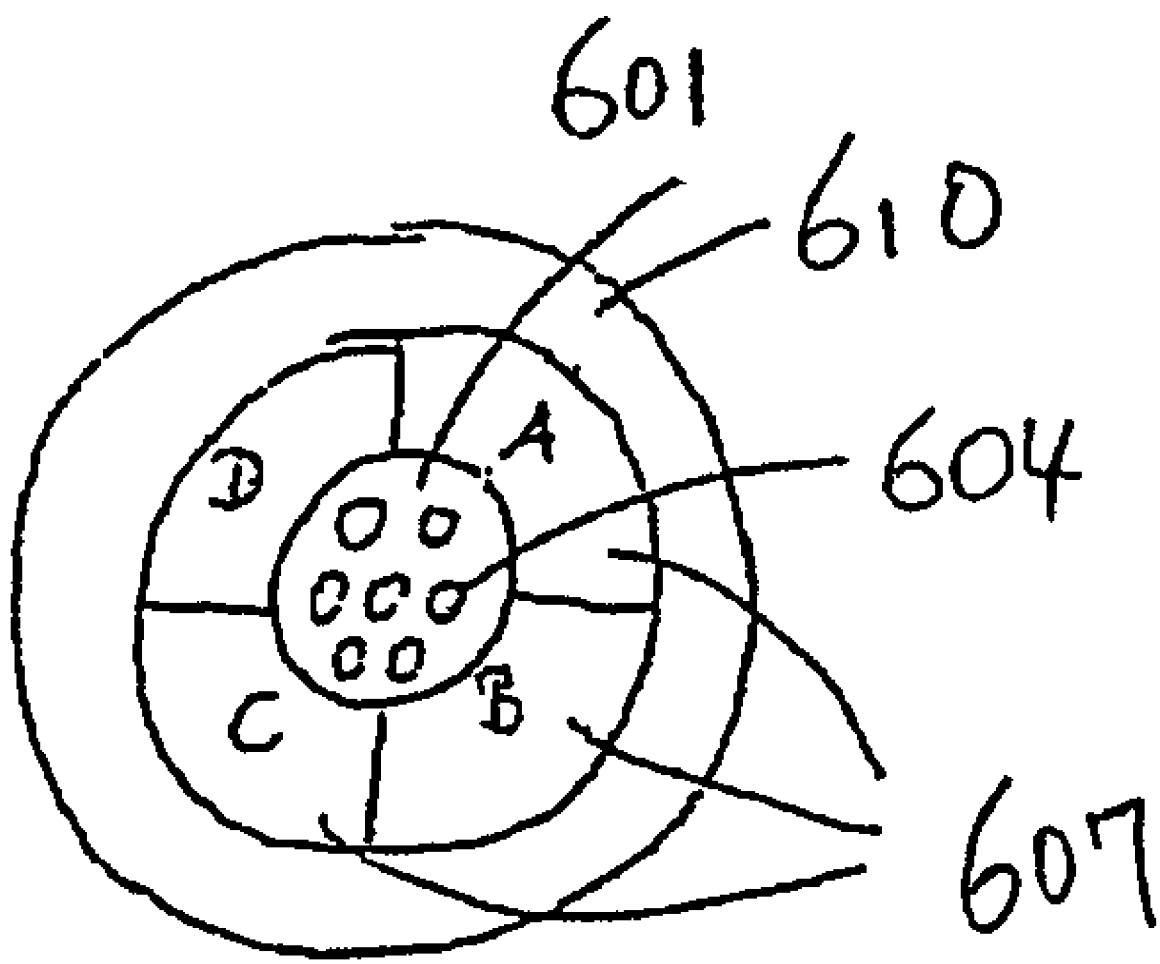
FIG. 10 provides a cross-sectional view of the catheter of FIG. 9, in an embodiment in which a plurality of control elements for x-ray absorption control are azimuthally structured into a plurality of sections.

FIG. 10 provides a cross-sectional view of the catheter of FIG. 9, in an embodiment in which the control elements for x-ray absorption control are azimuthally structured. In the illustrated embodiment, four x-ray absorption control elements are structured into four azimuthal sections, indicated as A, B, C, and D in FIG. 10, and disposed in between the inflatable element 610 and the catheter body 601. In this embodiment, different passageways can be provided for individually supplying the control media to the control elements, for individual x-ray absorption control.

These different passageways need not necessarily be operated while the probe in inserted in the patient. Rather, in one embodiment these passageways may be used only outside the patient, during the treatment preparation phase, in order to minimize the control elements during the actual treatment. In this embodiment, information regarding the desired radiation dose distribution must be known prior to the treatment, during the dose prescription process.

It should be understood that in other embodiments, different configurations and arrangements of the absorption control elements, as well as different arrangements of the tubes of the catheter, may be implemented.

While the x-ray brachytherapy system and method have been described and shown with reference to specific embodiments, it should be understood by those skilled in the art that various changes in form and detail may be made therein. Many other embodiments are possible.

Other embodiments are within the following claims.

What is claimed is:

1. An apparatus for applying x-rays to an interior surface of a body cavity, said apparatus comprising:
   A) a catheter assembly, including:
      a) a catheter body member extending from a proximal end onto a distal end, the catheter body member defining two or more interior channels between said proximal end and said distal end; and
      b) two or more inflatable elements affixed to said catheter body member at points along said catheter body member, and defining and inner region disposed about said catheter body member and an outer region disposed about said inner region, said inflatable element elements when inflated defining a predetermined surface contour;
   B) one or more flexible probe assemblies, each flexible probe assembly slidably positionable within at least one of said interior channels, each probe assembly including a transmission path having a proximal end and a distal end, said transmission path being adapted for transmitting an activating energy, which is incident on said proximal end, to said distal end;
   C) an x-ray generator assembly coupled to a distal end of each probe assembly, the x-ray generator assembly including an x-ray source configured to generate x-ray radiation
   wherein at least one of said inflatable elements is filled with a radiation absorbing fluid to control absorption of said generated x-ray radiation;
   wherein said two or more interior channels are each adapted to receive one or more of said flexible probe assemblies.

2. An apparatus in accordance with claim 1, wherein said x-ray source comprises:
   a) an electron source, responsive to the activating energy transmitted to said distal end of said transmission path, for generating electrons;
   b) an associated target element including at least one x-ray emissive material adapted to emit x-rays in response to incident accelerated electrons from said electron source.

3. An apparatus in accordance with claim 2, further comprising means for providing an accelerating voltage between each electron source and its associated target element so as to establish an accelerating electric field which acts to accelerate electrons emitted from said electron source toward said target element.

4. An apparatus in accordance with claim 2, wherein the x-ray generator assembly further comprises:
   a substantially rigid capsule configured to provide a housing for the electron source and the target element therewithin, the capsule defining a substantially evacuated interior region.

5. An apparatus in accordance with claim 2, further comprising an integrated control system, the integrated control system including at least one of:
   a) a voltage controller for a power supply configured to provide an accelerating voltage between each electron source and its associated target element;
   wherein the voltage controller is selectively operable to activate and de-activate the power supply and to control the magnitude and duration of said accelerating voltage;
   b) an optical controller for an optical source configured to generate optical radiation directed to said proximal end of said transmission path;
   wherein the optical controller is selectively operable to activate and de-activate the optical source and to control the intensity and duration of said optical source;
   c) a pressure controller configured to control the pressure of the catheter assembly;
   d) an inflation controller configured to control the inflation and deflation of the one or more inflation elements;
   e) a treatment planning system configured to control at least one of the direction, intensity, and duration of the x-rays generated by the x-ray source; and
   f) an interface to one or more external diagnostic systems.

6. An apparatus in accordance with claim 1, wherein said catheter comprises substantially rigid material.

7. An apparatus in accordance with claim 1, wherein said catheter comprises a substantially flexible material.

8. An apparatus in accordance with claim 1, wherein said catheter is characterized by at least one of: a substantially cylindrical configuration, and a substantially conical configuration.

9. An apparatus in accordance with claim 1, wherein each flexible probe is slidably positionable within at least one interior channel at one or more predetermined locations along said interior channel.

10. An apparatus in accordance with claim 1, wherein at least one flexible probe is slidably positionable within at least one interior channel along one or more variable locations along said at least one interior channel.

11. An apparatus in accordance with claim 1, wherein said inflatable element comprises a substantially resilient material.

12. An apparatus in accordance with claim 1, wherein said inflatable element, when inflated, defines a surface contour.

13. An apparatus in accordance with claim 12, wherein the inflatable element is shaped and configured so that its exterior surface is adapted to contact the interior surface of the body cavity, when said inflatable element is inflated from within said body cavity.

14. An apparatus in accordance with claim 1, wherein said electron source comprises a thermionic cathode.

15. An apparatus in accordance with claim 1, wherein the transmission path is configured to transmit optical radiation, and wherein the activating energy comprises optical radiation that causes thermionic emission of electrons from said thermionic cathode, when incident upon said cathode.

16. An apparatus in accordance with claim 15, wherein the transmission path comprises an optical fiber.

17. An apparatus in accordance with claim 16, wherein the optical source comprises at least one of: a diode laser; an Nd:YAG laser; an Nd:YVO$_4$ laser; a molecular laser; an LED (light emitting diode); an OLED (organic light emitting diode); and an SLED (superluminescent light emitting diode).

18. An apparatus in accordance with claim 15, further comprising an optical source configured to generate optical radiation directed to said proximal end of said transmission path.

19. An apparatus in accordance with claim 1, further comprising on or more interior passageways extending within the catheter from points at or near the proximal end of the catheter body member to points at or near the distal end of the catheter body member, each passageway being in communication with an interior region of at least one inflatable element;
   wherein each passageway is configured to transport at least one control medium from outside the catheter to an interior region of the at least one inflatable element so that the inflation or deflation of the at least one inflatable element can be controlled by selective delivery of the control medium to the interior region.

20. An apparatus in accordance with claim 19, wherein said control medium comprises a fluid.

21. An apparatus in accordance with claim 20, wherein said fluid comprises a fluid adapted to control absorption to shape the field of the x-ray radiation from the x-ray source in accordance with a radiation distribution pattern specified by a prescribed isodose surface.

22. An apparatus in accordance with claim 20, wherein said fluid comprises at least one of: air; water; a solution of natrium chloride.

23. An apparatus in accordance with claim 19, wherein one or more of the passageways is configured to transport at least one of a cooling fluid and a heating fluid.

24. An apparatus in accordance with claim 1, further comprising a position controller for controlling at least one of the position of the catheter assembly and the position of the one or more flexible probe assemblies.

25. An apparatus in accordance with claim 24, wherein said position controller comprises an imaging system configured to view the catheter assembly and the flexible probe assemblies.

26. An apparatus in accordance with claim 25, wherein said imaging system comprises an ultrasound imaging system.

27. An apparatus in accordance with claim 1, further comprising an x-ray dose controller configured to control the dose of radiation delivered by each flexible probe.

28. An apparatus in accordance with claim 1, further comprising a layer surrounding the body member and including x-ray absorptive material.

29. An apparatus in accordance with claim 1, wherein the body member includes one or more alignment marks.

30. An apparatus in accordance with claim 1, further comprising a rotatable mount for the x-ray generator assembly.

31. An apparatus in accordance with claim 1 wherein said first inflatable element includes divides said inner region into at least two azimuthal sections.

32. An apparatus in accordance with claim 31 further comprising a plurality of passageways in said catheter body member, each of said passageways being coupled to an associated one of said sections and being adapted for selective filling of said associated section with said fluid.

33. An apparatus in accordance with claim 1 wherein said first inflatable element includes divides said inner region into at least two azimuthal sections.

34. An apparatus in accordance with claim 33 further comprising a plurality of passageways in said catheter body member, each of said passageways being coupled to an associated one of said sections and being adapted for selective filling of said associated section with said fluid.

35. An apparatus according to claim 1 wherein said probe is flexible.

36. An apparatus in accordance with claim 1 wherein at least one said inflatable element is filled with a radiation absorbing fluid to control absorption of said generated x-rays.

37. An apparatus in accordance with claim 36 wherein at least two of said inflatable element are filled with a radiation absorbing fluid to control absorption of said generated x-rays.

38. An apparatus for applying x-rays to an interior surface of a body cavity, said apparatus comprising:
  A) a catheter assembly, including:
    a body member extending from a proximal end onto a distal end and defining two or more interior channels, each interior channel extending between points at or near said proximal end and points at or near said distal end,
    at least one inner tube enclosing the body member, said inner tube being inflatable to define an inner region disposed about said body member, and at least one outer tube having a diameter greater than and disposed about the inner tube, said outer tube being inflatable to define an outer region disposed about said inner region, and
    one or more inflatable elements disposed between said inner and outer tubes and coupled to said inner tube at points along said inner tube;
    wherein each inflatable element of said inner tube and said outer tube, when in an inflated state, define a surface contour;
  B) one or more flexible probe assembles, each flexible probe assembly slidably positionable within at least one of the interior channels, each probe assembly including a transmission path adapted to transmit an activating energy, which is incident on a proximal end of the path, to a distal end of the path;
    and
  C) an x-ray generator assembly coupled to a distal end of each probe assembly, the x-ray generator assembly including an x-ray source for generating x-rays;
  wherein said two or more interior channels are each adapted to receive on or more of said flexible probe assemblies.

39. An apparatus in accordance with claim 38, wherein said inner tube and said outer tube are disposed in a concentric configuration relative to each other.

40. An apparatus in accordance with claim 38, further comprising an inflation controller configured to control the inflation and deflation of the at least one inner tube.

41. An apparatus in accordance with claim 38 wherein at least one said inflatable element is filled with a radiation absorbing fluid to control absorption of said generated x-rays.

42. An apparatus in accordance with claim 41 wherein at least two of said inflatable element are filled with a radiation absorbing fluid to control absorption of said generated x-rays.

43. An apparatus according to claim 38 wherein said probe is flexible.

* * * * *